United States Patent [19]

Paolino, (widow of Francis Meilland)

[11] Plant 4,037

[45] Apr. 5, 1977

[54] ROSE PLANT — MEIRODIUM VARIETY

[76] Inventor: Marie-Louis Paolino, (widow of Francis Meilland), c/o Meilland & Cie, Societe en nom collectif, 134 boulevard du Cap, Antibes (Alpes Maritimes), France

[21] Appl. No.: 658,710

[22] Filed: Feb. 17, 1976

[30] Foreign Application Priority Data

Feb. 20, 1975 France ..... 75.00915
June 18, 1975 Italy ..... 24488/75

[51] Int. Cl.[2] ..... A01H 5/00
[52] U.S. Cl. ..... Plt./20
[58] Field of Search ..... Plt./20–21

*Primary Examiner*—Robert E. Bagwill
*Attorney, Agent, or Firm*—Burns, Doane, Swecker & Mathis

[57] ABSTRACT

A rose plant of the Hybrid Tea Class, with double flowers which are blood red on the inside and cardinal red on the outside, wherein the seed parent was the result of the pollination of the variety TANorstar by the variety MEIalto, and the pollen parent was the result of the pollination of an unnamed variety born of a crossing between the variety MEIbrem and the variety MEIalfi by the variety TANorstar.

11 Drawing Figures

The object of the present invention is a variety of rose-plant of the Hybrid Tea Class, with Blood red double flowers, which is distinguishable from varieties already known in this Class and this kind of color, on account of the following characteristics:

The Blood red color of the flowers is quite original.

Very vigorous plant, with an excellent aptitude to forcing, and a yield of full blooms, with very long stems.

In view of the characteristics mentioned above, the present invention answers the needs of the horticultural industry for all uses, and especially for the production of cut flowers under glass.

The variety which is the object of the present invention owes its creation to an operation of artificial pollination where two genitors were brought together, whose previous and respective study had allowed to anticipate, in their common descent, the appearance of the characters sought for.

The rose-plant chosen as female genitor (seed parent) was the result of the pollination of the variety TANorstar by the variety MEIalto; that chosen as male genitor was the result of the pollination of an unknown variety born of a crossing between the variety MEIbrem and the variety MEIalfi, by the variety TANorstar.

The operation of artificial pollination thus performed can therefore be expressed by the following schematic formula:

[TANorstar × MEIalto] × [(MEIbrem × MEIalfi) × TANorstar]

From the fruits formed after this controlled pollination, seeds were extracted whose cells resulted from the combination of factors which existed in the cells of the genitors and in virtue of which these genitors had precisely been chosen.

Seeds were sown and 420 small plants were obtained. They were physically and biologically distinct from one another.

After having eliminated all the plants which were abnormal or deficient, or whose characters were too remote from the ones that were sought for, the grafting of the remaining plants was proceeded with, in order to carry on the work on rose-plants which were, in every respect, in conformity with those produced and commercialized by the professional nurserymen.

This rose-plant was producing double flowers, Blood red inside and Cardinal red on the outside; it was very vigorous and gave out full flowers on long stems.

Technical tests (grafting inside or outside, with started eye-buds, dormant eye-buds on different understocks, in heated glass-houses, cold glass-houses, etc.) were then made in order to ascertain the behavior and the yield-capacity of the variety just created. The results were conclusive and underlined the importance of creating this new variety with a view to its industrial exploitation, for all uses, and especially for the production of cut flowers.

BRIEF DESCRIPTION OF THE DRAWINGS

In order to allow of the identification of this hybrid tea rose-plant with double flowers, Blood red inside and Cardinal Red outside, there is attached to this description, as a sample, a photographic reproduction of the distinctive elements of the plant and of its flower, representing.

Figures 1, 2, 3, 4, 5, 6, 7, 8, 9, 10, 11:
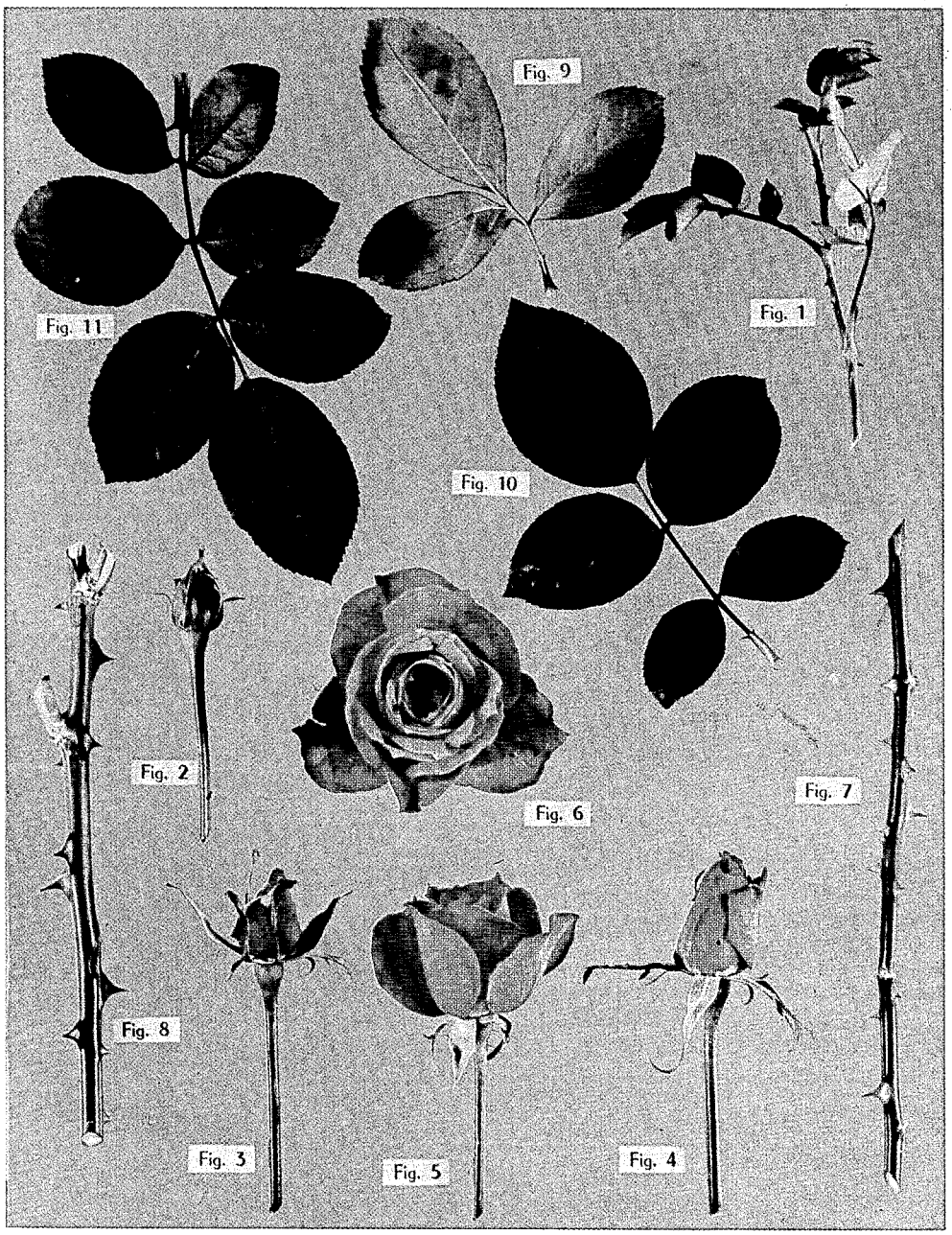
FIG. 1 — a specimen of a young shoot.
FIG. 2 — a specimen of a bud before the opening of the sepals.
FIG. 3 — a specimen of a bud when sepals open.
FIG. 4 — a specimen of a bud when the first petal opens.
FIG. 5 — a specimen of a flower in the course of opening.
FIG. 6 — a specimen of a flower fully open, flat view, upper surface.
FIG. 7 — a portion of a flowering stem.
FIG. 8 — a portion of a main branch.
FIG. 9 — a specimen of leaf with 3 folioles, under side.
FIG. 10 — a specimen of leaf with 5 folioles, upper side.
FIG. 11 — a specimen of leaf with 7 folioles, upper side.

The characters and properties of the new variety, obtained as indicated above, are strictly transmissible by agamic means, also called "asexual means", i.e. by any means of vegetative propagation, and in particular by grafting an "eye" which will be called in the trade by the name of Meirodium 0897 F and which will be found on industrial plants as well as on cut stems delivered subsequently in the trade. Thus will be obtained once again the rose variety which is the object of the patent, and whose botanical and descriptive characteristics, noted on plants under glass, grown at Cap d'Antibes, Alpes-Maritimes, France, are detailed below:

DESCRIPTION — Plant Under Glass

The Chart used for the identification of the colors is that of the Royal Horticultural Society (R.H.S. Color Chart). The terminology preceding the numbered references, proper to this Chart, has been added to designate, in common terms, the corresponding colors.

Class: Hybrid Tea.

Plant:

*Height.*—On the basis of the cutting back of the plants to about 0 m 85, the length of the flowering stems to be cut can be said to be between 60 and 80 cms. (total: 1m 45/1m 65).

*Habit.*—Straight.

Branches:

*Color.*—Young stems: before buds are formed, the young stems are reddish purple on the side exposed to the sun, and light green on the shady side; the first leaves are reddish purple (common terms). Mature wood: lettuce green 144/A (yellow green group).

*Prickles.*—Shape: Upper edge — slightly concave. Lower edge — concave. Base — elliptical. Size: medium. Quantity: average. Color: on young stems — reddish purple (common term). On mature wood — straw, then havana brown (common terms).

Leaves:

*Stipules.*—Dentate, pectinate, fairly long and moderately wide.

*Petiole.*—Obverse: light green groove, edges fairly glandular. Reverse: light green, stained with reddish purple, even in the adult foliage. Fairly numerous hooked prickles.

*Folioles.*—Number — 3 — 5 — fairly often 7. Shape: oval, rounded base which can be very slightly asymmetrical. Wide and symmetrical tip. Teeth: single and fine. Texture: leathery. General effect: generally ample foliage, semi-dull and moderately dense. Color: young foliage — upper surface — yellowish green 144/A (yellow green group) very widely suffused with medium green 137/A (green group); under surface — light green 191/B (greyed green group, widely suffused with reddish purple; adult foliage — upper surface: dark green 147/A (yellow green group); under surface: greyish green 191/B (greyed green group).

Inflorescence:

*Number of flowers.*—One flower per stem.

*Peduncle.*—Fairly long, 10 cms. average, erect, rigid. With small acicules. Light green — It can be slightly reddish towards the tip.

*Sepals.*—Hairy and whitish inside, yellowish green and smooth outside. 45 mm. × 12 mm. fairly wide at base, with a narrow and tapered tip. They can show a few appendages.

*Bud.*—Shape: oval. Length: 40 mm. outside the calyx, width 28 mm. Size: medium. Color: when opening — inside — currant red 46/A (red group); outside — Currant red 46/A (red group) suffused with 53/A on the edge of the petals and along the median vein.

*Flower.*—Form: first of all, high-centered, overlapping petals, then fully open as a cup, the outside petals being more or less wavy. Double flower — diameter: 10/12 cms. on an average. Color: when opening — inside — Currant red 46/A (red group); outside — Currant red (red group) suffused with 53/A (red group) on the edge of the petals and along the median vein. During the course of opening — inside: Blood red 45/A (red group). Yellow unguis; outside: Cardinal red 53/B (red group) widely suffused with Crimson red. When fully open — inside: Blood red 45/B (red group) suffused with Crimson red; outside: Cardinal red 53/B (red group). Fragrance: very light. Long lasting quality: Corolla — petals — texture — very firm; shape — widely rounded; edges more or less wavy. They can be slightly indented. Some of the first outside petals can show a median vein, greenish and hairy, more or less pronounced on the inside. Number: 40/45 on an average. The petals drop off cleanly.

*Stamens.*—Number — 150 average; anthers — normal, yellow. They reach over the level of the stigmas; filaments — yellowish at base, becoming crimson red at the top. Pistils — number: 180 average; stigmas: pale yellow; styles: short, yellowish, and hairy at base, light purple at tip. receptacle — light green, smooth, fairly wide and cup-shaped.

Development

*Vegetation.*—Very vigorous.

*Flowering.*—Practically continuous under glass.

*Resistance to diseases.*—Good.

I claim:

1. A new and distinct variety of hybrid tea rose-plant of vegetative reproduction, characterized by the fact that, from the physical point of view, the plant with lettuce green adult wood, is erect, the flower is double, Blood red on the inside and cardinal red on the outside, the petals are firm and show a yellow unguis;

from the biological point of view, this rose-plant is of vigorous vegetation, blooms practically continuously, its flowers last a long time, and its petals drop off cleanly substantially as shown and described.

* * * * *